(12) United States Patent
Salama et al.

(10) Patent No.: US 12,295,366 B2
(45) Date of Patent: *May 13, 2025

(54) PRESERVATION OF PERSONAL CARE COMPOSITIONS

(71) Applicant: SHARON LABORATORIES LTD., Ashdod (IL)

(72) Inventors: Paul Salama, Ashdod (IL); Ariel Gliksberg, Ashdod (IL)

(73) Assignee: SHARON LABORATORIES LTD., Ashdod (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/235,855

(22) Filed: Aug. 20, 2023

(65) Prior Publication Data

US 2024/0008486 A1    Jan. 11, 2024

Related U.S. Application Data

(63) Continuation of application No. 16/978,705, filed as application No. PCT/IL2019/050257 on Mar. 7, 2019, now Pat. No. 11,771,084.

(Continued)

(51) Int. Cl.
*A01N 43/16* (2006.01)
*A01N 25/02* (2006.01)
(Continued)

(52) U.S. Cl.
CPC ............. *A01N 43/16* (2013.01); *A01N 25/02* (2013.01); *A01N 25/04* (2013.01); *A01N 25/12* (2013.01); *A01N 25/22* (2013.01); *A01N 25/30* (2013.01); *A01N 33/12* (2013.01); *A01N 47/28* (2013.01); *A61K 8/416* (2013.01); *A61K 8/498* (2013.01);
(Continued)

(58) Field of Classification Search
CPC ........ A01N 25/12; A01N 25/04; A01N 25/22; A01N 25/30; A01N 47/28; A01N 25/02; A01N 33/12; A61K 8/44; A61K 8/498; A61K 2800/524; A61K 47/26; A61K 31/351; A61K 8/4973; A61K 8/84; A61Q 5/02; A61Q 5/12; A61Q 19/10; A61P 31/04

See application file for complete search history.

(56) References Cited

U.S. PATENT DOCUMENTS 6,344,218 B1 * 2/2002 Dodd .................. A61Q 15/00
424/605
2002/0061832 A1    5/2002 Reinehr et al.
(Continued)

FOREIGN PATENT DOCUMENTS

WO    2017164627 A2    9/2017

OTHER PUBLICATIONS

PCT Search Report for International Application No. PCT/IL2019/050257 mailed Sep. 12, 2019, 5 pp.
(Continued)

*Primary Examiner* — Jianfeng Song
(74) *Attorney, Agent, or Firm* — The Roy Gross Law Firm, LLC; Roy D. Gross (57) ABSTRACT

Formulations comprised of pyrone and a mixture of at least one cationic surfactant, such as for preservation of personal care compositions, are disclosed. Articles comprising the formulations are further disclosed.

10 Claims, 2 Drawing Sheets

Related U.S. Application Data (60) Provisional application No. 62/640,105, filed on Mar. 8, 2018.

(51) Int. Cl.
| | |
|---|---|
| *A01N 25/04* | (2006.01) |
| *A01N 25/12* | (2006.01) |
| *A01N 25/22* | (2006.01) |
| *A01N 25/30* | (2006.01) |
| *A01N 33/12* | (2006.01) |
| *A01N 47/28* | (2006.01) |
| *A61K 8/41* | (2006.01) |
| *A61K 8/49* | (2006.01) |
| *A61K 8/84* | (2006.01) |
| *A61Q 5/02* | (2006.01) |
| *A61Q 19/10* | (2006.01) |

(52) U.S. Cl.
CPC .............. *A61K 8/84* (2013.01); *A61Q 5/02* (2013.01); *A61Q 19/10* (2013.01); *A61K 2800/524* (2013.01)

(56) References Cited

U.S. PATENT DOCUMENTS

| | | | |
|---|---|---|---|
| 2002/0173436 A1* | 11/2002 | Sonnenberg | C11D 13/14 510/141 |
| 2008/0207481 A1* | 8/2008 | Meine | C11D 17/06 512/20 |
| 2010/0028325 A1 | 2/2010 | Rocabayera Bonvila et al. | |
| 2013/0344120 A1 | 12/2013 | Scott et al. | |

OTHER PUBLICATIONS

PCT Written Opinion for International Application No. PCT/IL2019/050257 mailed Sep. 12, 2019, 8 pp.

Preliminary Report on Patentability for International Application No. PCT/IL2019/050257 dated Sep. 8, 2021, 9 pp.

Ziklo Noa: "Antimicrobial Action of Maltol", Scholarly Community Encyclopedia: Biotechnology & Applied Microbiology, Sep. 27, 2021, pp. 1-9. Retrieved from the Internet: URL:https://encyclopedia.pub/item/download_pdf/02ec83d9e1ad499ac665d70e13653730.

* cited by examiner

PRESERVATION OF PERSONAL CARE COMPOSITIONS

CROSS REFERENCE TO RELATED APPLICATIONS

This application is a continuation of U.S. patent application Ser. No. 16/978,705 filed Sep. 6, 2020, which is a National Phase of PCT Patent Application No. PCT/IL2019/050257 having International filing date of Mar. 7, 2019, which claims the benefit of priority to under 35 U.S.C. § 119(e) of U.S. Provisional Patent Application No. 62/640,105 filed Mar. 8, 2018, entitled "PRESERVATION OF PERSONAL CARE COMPOSITIONS", the contents of which are all incorporated herein by reference in their entirety.

FIELD OF INVENTION

The present invention is in the field of preservation of personal care formulations.

BACKGROUND OF THE INVENTION

Antimicrobial compositions are used, for example, in the health care industry, food service industry, meat processing industry, and in the private sector by individual consumers.

Preservation of personal care products from microbial contamination has become a difficult task since the available approved antimicrobials are very few and those which have good antimicrobial activity are quite toxic. Consumers seek for products for topical applications being free from toxic antimicrobials that can be used as preservatives.

Infection is a constant risk to any healthy person, and poses even a higher risk to hospitalized patients. The risk of infection is further increased when the natural infection barriers of skin or other epithelial surfaces are breached during a surgical procedure, and/or otherwise in cases where bacteria normally present on the skin or in the air are allowed to access the interior surfaces of the body.

Hospital-acquired (nosocomial) infections occur even when good hygiene and sterile technique is followed, although the incidence is reduced. Despite even the most rigorous aseptic procedures, people cannot be completely isolated from infectious agents.

The widespread use of antibacterial compositions indicates the importance consumers place on controlling bacteria and other microorganism populations on skin. It is important, however, that antibacterial compositions provide a substantial and broad-spectrum reduction in microorganism populations quickly and without problems associated with toxicity and skin irritation. In particular, antibacterial cleansing compositions typically contain an active antibacterial agent, a surfactant, and various other ingredients, for example, dyes, fragrances, pH adjusters, thickeners, and the like, in an aqueous carrier.

Despite being successful in controlling or eliminating bacterial infections, widespread use of antibiotics both in human medicine and as a feed supplement in poultry and livestock production has led to drug resistance in many pathogenic bacteria. The evolution and spread of resistance genetic determinants, multidrug resistant (MDR) bacteria that cause life-threatening infections have been increasingly emerged, and as such, the effectiveness of antibiotics has greatly diminished in the last decade. Furthermore, as resistance spreads among bacteria, there is great concern that antibiotics treatment will become increasingly less effective and, in some cases, completely ineffective.

Nosocomial infections caused by antibiotic-resistant bacteria result in patient suffer and mortality and impose a substantial burden on the medical system due to extended periods of hospitalization. The economic impact of managing infections caused by nosocomial infections is substantial, and costs are estimated to be more than $4 billion annually.

Currently, a number of blends are available for preservation of personal care products where synergy between antimicrobials is exploited in lowering the concentration of individual ingredient. Another great advantage is that the microbes cannot develop resistance very easily if they are attacked by a combination of antimicrobials.

SUMMARY OF THE INVENTION

According to one aspect, the present invention provides a composition comprising a pyrone and at least one cationic surfactant in a ratio of at least 70:30 by weight, respectively.

In some embodiments, the ratio of pyrone/cationic surfactant ranges from 85:15 to 99:1 by weight, respectively.

In some embodiments, the pyrone is selected from the group consisting of maltol, ethyl maltol or any derivative thereof.

In some embodiments, the at least one cationic surfactant is a tertiary ammonium compound.

In some embodiments, the at least one cationic surfactant is a quaternary ammonium compound.

In some embodiments, the at least one cationic surfactant is a mixture of at least one tertiary ammonium compound and at least one quaternary ammonium compound.

In some embodiments, the at least one cationic surfactant is a mixture of at least two quaternary ammonium compounds.

In some embodiments, the at least one quaternary ammonium compound is a monomeric compound.

In some embodiments, the at least one quaternary ammonium compound is a polymeric compound.

In some embodiments, the ratio between the quaternary ammonium compounds ranges from 10:1 to 1:10.

According to another aspect, there is provided a composition comprising maltol and at least two cationic surfactants.

In some embodiments, the quaternary ammonium is selected from the group consisting of: benzyldimethyldodecylammonium chloride, didecyldimethylammonium chloride, dodecyltrimethylammonium chloride, hexadecyltrimethylammonium chloride, Polyquaternium-2, Polyquaternium-80, Polyquaternium-11, Polyquaternium-52, Polyquaternium-17, Sodium Cocamidopropyl PG-Dimonium Chloride Phosphate (Cola Lipid C), Laurdimoniumhydroxypropyl decylglucoside chloride (SugaQuat L-1010), Berberine, Berberrubine, *Berberis vulgaris* root extract, Isopropylbenzyl butylnorberberine iodide, Palmatine, Jatrorrhizine, Coptisine, Ungeremine, Epiberberine, Pseudoberberine, Stepharanine, Sinapine, or any combination thereof.

In some embodiments, the formulation is an antimicrobial formulation.

In some embodiments, the formulation is for use in the treatment of a medical, cosmetic and/or cosmeceutical condition.

In some embodiments, the formulation further comprises a chelating agent, or a salt thereof.

In some embodiments, the formulation further comprises 0.1% to 10% (w/w) of the chelating agent, or a salt thereof.

In some embodiments, the chelating agent is selected from the group consisting of: Disodium EDTA—Ethylenediaminetetraacetic acid disodium salt, EDTMP—Ethylenediamine tetra (methylene phosphonic acid), Alanine di-acetic acid, Ascorbic acid, Sodium Gluconate, Zinc gluconate, Vanillin, Ethylenediamine-N,N-discuccinic acid trisodium salt (Natrlquest E30), pentetic acid (DTPA), and any combination thereof.

According to another aspect, there is provided an article comprising the disclosed formulation in any embodiment thereof.

In some embodiments, the article is a personal care product.

In some embodiments, the article is selected from the group consisting of: a fabric, a bandage, a wipe, a pledget, a swab, a suppository, a dressing, a solution, a mousse, a pad, and a patch.

In some embodiments, the product comprises a formulation in the form selected from the group consisting of: paste, cream, lotion, foam, gel, emulsion, an ointment, and soap.

In some embodiments, the article is for use in the treatment of a condition selected from medical, cosmetic and cosmeceutical condition.

According to another aspect, there is provided a method of inhibiting or reducing the formation of load of a microorganism in and/or on an article, the method comprising contacting the article with the disclosed formulation in an embodiment thereof.

In some embodiments, the microorganism is selected from bacteria, molds and fungi.

In some embodiments, the bacteria are Gram-positive bacteria selected from the group consisting of: *Staphylococcus aureus, Staphylococcus epidermidis*, and *Bacillus cereus*; or Gram-negative bacteria selected from the group consisting of: *Escherichia coli* and *Pseudomonas aeuruginosa*.

In some embodiments, the fungi are *Candida albicans*.

In some embodiments, the mold is *Aspergillus niger*.

According to another aspect, there is provided a method of preserving a cosmetic product, comprising adding to the cosmetic product the disclosed formulation in an embodiment thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

The present invention, in some embodiments thereof, relates to compositions and, more particularly, but not exclusively, to personal care compositions exhibiting antimicrobial (also referred to as "anti-micro-organic") activity, articles containing same, and uses thereof in, for example, reducing or preventing growth of microorganisms.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

High quality antimicrobial compositions are desirable as they provide a good solution to biofouling and/or infection processes and/or formation of biofilms on a surface. Conventional personal care compositions present several drawbacks, as many of these compositions are referred to as being toxic (or releasing toxic materials to the environment), instable, inefficient or are limited in preventing (or complete diminishing) microorganism growth, expensive and produced via complicated manufacturing processes which at times require expensive equipment for their manufacture.

Herein throughout, by "composition" it is further meant to refer to a formulation.

The present inventors have designed non-toxic antimicrobial formulations (also referred to as "blends").

According some embodiments of the present invention, there is provided a composition comprising a compound comprising a pyrone and at least one cationic surfactant.

In some embodiments, the pyrone is maltol.

In some embodiments, the pyrone is a maltol derivative wherein derivative refer to a pyrone having at least 80% antimicrobial activity similar to maltol combined with the at least one cationic surfactant, as disclosed herein.

In some embodiments, the cationic surfactant is a natural product-derived cationic surfactant.

In some embodiments, the cationic surfactant is quaternary ammonium.

In some embodiments, the cationic surfactant is a natural product-derived quaternary ammonium.

In some embodiments, a formulation as described herein is a 100% natural product-derived antimicrobial formulation.

In some embodiments, the quaternary ammonium is selected from, without being limited thereto, benzyldimethyldodecylammonium chloride, didecyldimethylammonium chloride, dodecyltrimethylammonium chloride, hexadecyltrimethylammonium chloride, Polyquaternium-2, Polyquaternium-80, Polyquaternium-11, Polyquaternium-52, Polyquaternium-17, Sodium Cocamidopropyl PG-Dimonium Chloride Phosphate (Cola Lipid C), Laurdimonium-hydroxypropyl decylglucoside chloride (SugaQuat L-1010), Berberine, Berberrubine, *Berberis vulgaris* root extract, Isopropylbenzyl butylnorberberine iodide, Palmatine, Jatrorrhizine, Coptisine, Ungeremine, Epiberberine, Pseudoberberine, Stepharanine, Sinapine, and any combination thereof.

In some embodiments, maltol and a quaternary ammonium are present at a ratio that ranges from 70:30 to 99:1, by weight, respectively. In some embodiments, maltol and a quaternary ammonium are present at a ratio that ranges from 70:30 to 99:1, 80:20 to 99:1, 80:20 to 90:10, 80:20 to 98:2, or 80:20 to 95:5, by weight, respectively, including any range therebetween.

As demonstrated in the Examples section that follows, the present inventors have shown that compositions (e.g., formulations) comprising a pyrone and a cationic surfactant, being at certain predetermined ratios, exhibit a desired stability as well as improved antimicrobial activities, compared to other compositions comprising different materials from the invented formulations or from formulations comprising the same materials but having different volume or weight ratios thereof.

As demonstrated in the Examples section that follows, the present inventors have shown that a specific ratio of the above-mentioned compounds impart the formulation with antimicrobial activities.

The present inventors have also shown that the disclosed formulation can be used to impart to articles the antimicrobial activities.

According some embodiments of the present invention there is provided a composition comprising maltol, and at least one cationic surfactant or salt thereof.

In some embodiments, the cationic surfactant and maltol are present at a ratio that ranges from 15:85 to 2:98, by weight, respectively.

According some embodiments of the present invention there is provided a composition comprising maltol, a first cationic surfactant and a second cationic surfactant.

In some embodiments, the first cationic surfactant is a quaternary ammonium. In some embodiments, the second cationic surfactant is a quaternary ammonium.

In some embodiments, a first cationic surfactant, a second cationic surfactant and maltol are present at a ratio of 2.5:2.5:95 to 5:5:90 by weight, respectively.

In some embodiments, a first cationic surfactant, a second cationic surfactant and maltol are present at a ratio of 1:1:95 to 5:5:90, 2:2:96 to 5:5:90, 2.3:2.3:95.4 to 5:5:90, 3:3:94 to 5:5:90, or 4:4:92 to 5:5:90, by weight, respectively, including any range therebetween.

In some embodiments, the formulation further comprises a chelating agent, or a salt thereof.

In some embodiments, the formulation further comprises 0.1% to 10% (w/w) of a chelating agent, or a salt thereof. In some embodiments, the formulation further comprises 0.1% to 9% (w/w), 0.1% to 8% (w/w), 0.1% to 7% (w/w), 0.1% to 6% (w/w), 0.1% to 5% (w/w), 0.2% to 10% (w/w), 0.3% to 10% (w/w), 0.5% to 10% (w/w), 1% to 10% (w/w), 0.2% to 7% (w/w), 0.3% to 7% (w/w), 0.5% to 7% (w/w), 1% to 7% (w/w), 0.2% to 5% (w/w), 0.3% to 5% (w/w), 0.5% to 5% (w/w), or 1% to 5% (w/w), of a chelating agent, or a salt thereof, including any range therebetween.

In some embodiments, the chelating agent is selected from the group consisting of: Disodium EDTA—Ethylenediaminetetraacetic acid disodium salt, EDTMP—Ethylenediamine tetra (methylene phosphonic acid), Alanine diacetic acid, Ascorbic acid, Sodium Gluconate, Zinc gluconate, Vanillin, Sodium vanillate, Ethylenediamine-N,N-discuccinic acid trisodium salt (Natrlquest E30), pentetic acid (DTPA), and any combination thereof.

As used herein, the term "chelating agent" refers to any organic or inorganic compound that will bind to a metal ion having a valence greater than one. "Chelating agents" include, but are not limited to, organic chelating agents or any other chelating agent that will chelate divalent ions such as $Ca^{2+}$, $Mg^{2+}$, $Mn^{2+}$, $Fe^{2+}$, and $Zn^{2+}$.

In some embodiments, a formulation according to the present invention comprising a chelating agent, or a salt thereof, has a superior stability than the corresponding formulation without a chelating agent, or a salt thereof.

In some embodiments, a formulation according to the present invention comprising a chelating agent, or a salt thereof, has a longer shelf live than the corresponding formulation without a chelating agent, or a salt thereof.

In some embodiments, a formulation according to the present invention comprising a chelating agent, or a salt thereof, preserves its color during manufacturing processes of a personal care product, as compared to the corresponding formulation without a chelating agent, or a salt thereof.

In some embodiments, the chelating agent, or a salt thereof may be used in an amount that is effective to bind the aforementioned metals (hereinafter alternatively referred to as an "effective amount"), typically an amount ranging from about 0.01% to about 10 weight % of the composition.

In some embodiments the cationic surfactant is a tertiary ammonium cation.

In some embodiments the tertiary ammonium cation is other than Ethyl Lauroyl Arginate.

In some embodiments the tertiary ammonium cation is other than formula (1) from patent application US20100028325A1.

In some embodiments, the cationic surfactant is a quaternary ammonium cation (also referred to as: "quat").

In some embodiments, the quaternary ammonium cation is positively charged polyatomic ion of the structure $NR_4^+$. In some embodiments, R is an alkyl group. In some embodiments, R is an aryl group. In some embodiments, the quaternary ammonium cation is derived from a quaternary ammonium salt. In some embodiments, the quaternary ammonium salt (e.g., benzyldimethyldodecylammonium, didecyldimethylammonium) comprises a counteranion.

In some embodiments, the quaternary ammonium cation and maltol are present at a ratio of at least 50:50 by weight, respectively.

As used herein, the term "alkyl" describes an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atoms, 22 carbon atoms, 23 carbon atoms, etc., up to and including 100 carbon atoms. In the context of the present invention, a "long alkyl" is an alkyl having at least 20 carbon atoms in its main chain (the longest path of continuous covalently attached atoms). A short alkyl therefore has 20 or less main-chain carbons.

The alkyl can be substituted or unsubstituted, as defined herein

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e. rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e. rings which share adjacent pairs of carbon atoms) groups having a completely conjugated pi-electron system. The aryl group may be substituted or unsubstituted, as indicated herein.

In some embodiments, the counteranion is halide. In some embodiments, the halide is chloride. In some embodiments, the halide is bromide.

In some embodiments, the counteranion is sulfonate. In some embodiments the sulfonate is mesylate.

In some embodiments, the formulation is a preservative e.g., for a personal care composition.

The formulation of the cationic surfactant is an emulsifier.

As used herein and in the art, the term "emulsifier" is intended to mean a surface-active agent that facilitates the mixing of two or more liquid substances that would separate into its component parts under normal conditions.

In some embodiments, the cationic surfactant provides detersive functionality to a formulation or act simply as wetting agents.

In some embodiments, the formulation is devoid of paraben. In some embodiments, the formulation is devoid of formaldehyde. In some embodiments, the formulation is devoid of formaldehyde and is further devoid of paraben.

In some embodiments, the formulation is not pH dependent.

In some embodiments of the present invention, the formulation further comprises a buffer solution or a pH adjuster to control the desired pH of the formulation.

As used herein, the terms "formulation", or "blend", which are used herein throughout interchangeably, refer to a vehicle composition in the form of emulsion, lotion, cream, gel etc., that optionally further comprises physiologically acceptable carriers and/or excipients and optionally other chemical components such as cosmetically, cosmeceutically or pharmaceutically active agents (e.g., drugs). The formulation can optionally further comprise a carrier, and optionally additional active agents and/or additives e.g., anti-freezing agents).

In some embodiments, the term "by weight" means by weight of the total composition.

As used herein, the term "physiologically acceptable" means approved by a regulatory agency of the Federal or a state government or listed in the U.S. Pharmacopeia or other generally recognized pharmacopeia for use in animals, and more particularly in humans.

Herein the term "excipient" refers to an inert substance added to a formulation as described herein to further facilitate processes and administration of the active ingredients.

The formulation of the invention can be prepared by any commonly used method for preparing a composition of materials. For example, the components of the formulations may be added and mixed together, or one of the components may be added to the other in the form of a solution which may, if desired, be evaporated or lyophilized after mixing for obtaining a homogeneous and stable solution or suspension.

In some embodiments, the disclosed composition, in any embodiment thereof, is a stable formulation.

As used herein the terms "stable formulation", or "long-lasting formulation", mean that the formulation remains in a state or condition of sufficient stability to have utility as a personal care agent, while maintaining the antimicrobial activity (with ±20% variation). For example, and without limitation, the formulation has a sufficient stability to allow storage at a convenient temperature, e.g., between 10° C. and 30° C., for a reasonable period of time of e.g., longer than one month, longer than three months, longer than six months, and longer than one year.

In some embodiments, the disclosed composition is incorporated into substrates susceptible to microbial growth as a preservative or a personal care system. For example, the preservative system may be incorporated into or be a personal care product, such as a shampoo, conditioner, cream, lotion, cosmetic, or soap; a household product, such as a fabric softener, laundry detergent, or hard surface cleaner.

In some embodiments, the disclosed composition is incorporated in a preservative or in a personal care system in a concentration (by total weight) of e.g., 0.1%, 0.5%, 1%, 1.5%, 2%, 2.5%, 3%, 3.5%, 4%, 4.5%, 5%, 5.5% 6%, 6.5%, 7%, 6.5%, 8%, 8.5%, 9%, 9.5% 10%, 10.5%, 11%, 11.5%, 12%, 12.5%, 13%, 13.5%, 14%, 14.5%, or 15%, including any value and range therebetween.

As used herein, the phrase "personal care" refers to compositions that can be formulated in various cosmetic and pharmaceutical consumer products utilizing a variety of delivery systems and carrier bases. Such consumer product forms include, but are not limited to, shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, Band-Aids, and balms.

In some embodiments, the disclosed formulation is in the form of, or a part of, a cream, an ointment, a paste, a gel, a lotion, a milk, an oil, a suspension, a solution, an aerosol, a spray, a foam, or a mousse.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols of varying molecular weight.

Lotions are preparations that are to be applied to the skin surface without friction. Lotions are typically liquid or semiliquid preparations in which solid particles, including the sunscreens-containing microcapsules, are present in a water or alcohol base. Lotions are typically preferred for covering/protecting large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

In some embodiment, the personal care system comprises an ionic formulation. In some embodiment, the personal care system comprises a cationic formulation. In some embodiment, the personal care system comprises a natural formulation.

Creams are viscous liquids or semisolid emulsions, either O/W or W/O. Cream bases are typically water-washable, and contain an oil phase, an emulsifier and an aqueous phase. The oil phase, also called the "internal" phase, generally comprises petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e. gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

Personal care formulations can further include, without limitation, human body or hair deodorizing solution, deodorizing gel, deodorizing spray, deodorizing stick, deodorizing roll-on, deodorizing paste, deodorizing cream, deodorizing lotion, deodorizing aerosol, and other commonly marketed human body and commonly marketed animal and pet deodorizing compositions.

Additional cosmetically or pharmaceutically beneficial (active) ingredients can also be included in the formulations of the present invention, which can be selected from, but are not limited to, skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In some embodiments of the present invention, the formulation is characterized by resistance to discoloration.

As used herein, "discoloration" is defined as change in the hue or in the visual appearance of a formulation, due to an internal reaction among its constituents or the bleaching or oxidation action caused by a combination of factors that include, but are not limited to, air, high temperature, humidity, ultraviolet exposure e.g., sunlight.

Articles Comprising the Formulations

According to an aspect of some embodiments of the present invention there is provided an article which comprises any one of the personal care formulation described herein.

Some embodiments of this aspect of present embodiments are included hereinabove, under "Exemplary Formulations", and form an integral part of embodiments relating to "Articles comprising the Formulation".

According to an aspect of some embodiments of the present invention, there is provided a pharmaceutical, cosmetic or cosmeceutical product comprising the formulation described in any of their respective embodiments herein, for use in treating a medical, cosmetic or cosmeceutic condition, as described herein.

According to an aspect of some embodiments of the present invention, the formulation described in any of their respective embodiments herein is used as, or a part of, a preservative in any pharmaceutical, cosmetic or cosmeceutical product or in any article as describe herein.

As used herein, "preservative" is used to prevent the growth of bacteria, fungi and/or molds in any personal care composition or formulation.

According to a further aspect of some embodiments of the present invention, there is provided a use of the formulation described herein in the manufacture of a pharmaceutical, cosmetic or cosmeceutical product, which can be used in treating a medical, cosmetic or cosmeceutic condition, as described herein.

In some embodiments, there is provided a method of treating a medical, cosmeceutical or cosmetic condition treatable by a topical or transdermal administration, the method comprising topically applying the formulation described herein (e.g., in the context of a pharmaceutical, cosmetic or cosmeceutic product) to a skin or mucosal tissue of a subject afflicted by the condition.

The phrases "topical" "topical administrations" and or any grammatical derivative thereof, is meant to encompass applications, which include, without limitation, dermal applications, ophthalmic application, vaginal application, rectal application and intranasal application.

Medical, cosmetic or cosmeceutical conditions that can benefit from containing the formulations described herein when applied topically, with or without an additional active ingredient, include, but are not limited to, infections caused by pathogenic microorganisms, as discussed in further detail hereinbelow, wounds, particularly when associated with an infection, acne, skin infections, viral blisters such as one caused by herpes, sexual dysfunction such as erectile dysfunction.

Hence, according to some embodiments of the present invention, the pharmaceutical, cosmetic or cosmeceutical formulation or product further comprises an antimicrobial agent, as an additional pharmaceutically active agent.

Microbial infections include any infection caused by a pathogenic microorganism, including, bacterial infection, fungal infection, protozoal infection, viral infection and the like, e.g., molluscum contagiosum (a viral infection of the skin or occasionally of the mucous membranes), fungal nail infections, and cutaneous leishmaniasis.

Topical bodily sites include skin, mucosal tissue, eye, ear, nose, mouth, rectum and vagina.

In some embodiments, there is provided an article (e.g., a medical device such as a bandage or adhesive patch), a formulation, or a product, as described herein, configured for topical application, whereby a condition treatable by such as article, product or formulation is an infection caused by a microorganism.

In some embodiments of the present invention, the article is e.g., a fabric, a bandage, a wipe (e.g., a wet wipe), a pledget, a swab, a suppository, a dressing, a solution, a mousse, a pad, or a patch.

In some exemplary embodiments of the present invention, the article is in the form of paste, cream, lotion, foam, gel, emulsion, an ointment, or soap.

In some embodiments, the personal care formulation of the present invention can be used to treat skin tissue or on damaged or unhealthy skin tissue.

The phrase "damaged or unhealthy skin tissue" as used herein refers to a deviation from healthy functional skin tissue. In the case of skin—a skin that is weaker, less elastic, and is more prone to injury than healthy skin. The structure of unhealthy or damaged skin is inferior to that of healthy skin (for example, the dermis and epidermis contain fewer cells and collagen).

The phrase "healthy skin tissue" as used herein refers to skin that is strong, elastic, smooth and plump. One purpose of treating healthy skin is to prevent deterioration of skin induced by aging or environmental stress including, but not limited to, microbial infection.

The term "damaged" as used herein, or any grammatical derivative thereof, refers broadly to injuries to the skin and subcutaneous tissue as well as internal organs initiated in any one of a variety of ways (e.g., pressure sores from extended bed rest, wounds induced by trauma, wounds received during or following a surgical procedure and the like) and with varying characteristics. Examples include, but are not limited to, bruises, scrapes, burn wounds, sunburn wounds, incisional wounds, excisional wounds, surgical wounds, necrotizing fascitis, ulcers, venous stasis ulcers, diabetic ulcers, decubitus ulcers, aphthous ulcers, pressure ulcers, scars, alopecia areata, dermatitis, allergic contact dermatitis, atopic dermatitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bullous pemphigoid, *Candida*, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Planus Like Keratosis, Lichen Simplex Chronicus, Lichen Sclerosus, Lymphomatoid Papulosis, Lupus of the Skin, Lyme Disease, Lichen *Striatus*, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, *Pityriasis* Lichenoides, *Pityriasis Rosea*, *Pityriasis Rubra* Pilaris, Plantar Warts, Poison Ivy, Poison Oak, *Pompholyx*, Pseudofolliculitis Barbae, Pruritus Ani and *Pityriasis* Alba.

Antimicrobial Activity

According to an aspect of some embodiments of the present invention there is provided a method of inhibiting or reducing or retarding the formation of load of a microorganism and/or the formation of a biofilm, in and/or on an article. The method comprises incorporating in and/or on the article any one of the formulations disclosed herein, including any of the respective embodiments thereof. The article can be any one of the articles described herein.

Such articles take advantage of the improved antimicrobial activity exhibited by the formulations as described herein.

In some embodiments, the components in the formulation act in synergism.

In some embodiments, the term synergism, or any grammatical derivative thereof, is defined as the simultaneous action of two or more compounds in which the total response of an organism to the combination is greater than the sum of the individual components. Although many combinations of antimicrobial compounds have been studied, a synergistic effect is rarely revealed and the global use of antimicrobial combinations with synergistically enhanced activity is rather limited.

Some embodiments of this aspect of present embodiments are included hereinabove, under "Exemplary Formulations", and under "Articles comprising the Formulation" and form an integral part of embodiments relating to "Antimicrobial Activity".

Herein "antimicrobial activity" is referred to as an ability to inhibit (prevent), reduce or retard bacterial growth, fungal growth, biofilm formation or eradicate living bacterial cells, or their spores, or fungal cells or viruses in a suspension or in a moist environment.

Herein, inhibiting or reducing or retarding the formation of load of a microorganism refers to inhibiting, reducing, or retarding growth of microorganisms and/or eradicating a portion or all of an existing population of microorganisms. Thus, formulations described herein can be used both in reducing the formation of microorganisms on or in an article, and in killing microorganisms in or on an article or a living tissue.

The microorganism can be, for example, a unicellular microorganism (prokaryotes, archaea, bacteria, eukaryotes, protists, fungi, algae, molds, yeast, euglena, protozoan, dinoflagellates, apicomplexa, trypanosomes, amoebae and the likes), or a multicellular microorganism.

An article, according to these embodiments, can be also a living tissue, for example, a skin or mucosal tissue, as described herein.

In the context of the present embodiments, the formulations, articles and methods described herein may be used to produce cell inhibiting surface, or a microbial cell killing surface, that remains active for extended periods. Such an antimicrobial surface may not need an additional treatment with antimicrobial compositions, clean-up treatments to effect decontamination and cosmetic painting, thereby simplifying upkeep of the physical condition and appearance of microbial infestation prone surfaces. It is contemplated that in some embodiments, the formulations of the present invention may be easily applied to susceptible surfaces in advance of and/or during exposure to a microbial organism.

In some embodiments, the microorganism comprises bacterial cells of bacteria such as, for example, Gram-positive and Gram-negative bacteria.

In some embodiments, the Gram-positive bacteria are *Staphylococcus aureus, Bacillus cereus* and *Staphylococcus epidermidis*.

In some embodiments, the Gram-negative bacteria are *Escherichia coli* and *Pseudomonas aeuruginosa*.

In some embodiments of the present invention, the microorganism is fungi e.g., *Candida albicans* and *Aspergillus niger*.

The term "biofilm", as used herein, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides.

In the context of the present embodiments, the living cells forming a biofilm can be cells of a unicellular microorganism (prokaryotes, archaea, bacteria, eukaryotes, protists, fungi, algae, euglena, protozoan, dinoflagellates, apicomplexa, trypanosomes, amoebae and the likes), or cells of multicellular organisms in which case the biofilm can be regarded as a colony of cells (like in the case of the unicellular organisms) or as a lower form of a tissue.

In the context of the present embodiments, the cells are of microorganism origins, and the biofilm is a biofilm of microorganisms, such as bacteria and fungi. The cells of a microorganism growing in a biofilm are physiologically distinct from cells in the "planktonic form" of the same organism, which by contrast, are single-cells that may float or swim in a liquid medium. Biofilms can go through several life-cycle steps which include initial attachment, irreversible attachment, one or more maturation stages, and dispersion.

The phrase "antibiofilm formation activity" refers to the capacity of a substance to affect the prevention of formation of a biofilm of bacterial, fungal and/or other cells, and/or to affect a reduction in the rate of buildup of a biofilm of bacterial, fungal and/or other cells, on a surface of a substrate. This activity is also referred to herein as anti-biofouling activity, or antifouling activity.

As used herein, the term "preventing" in the context of antimicrobial, indicates that the growth rate of the microorganism cells is essentially nullified or is reduced by at least 20%, at least 30%, at least 40%, at least 50%, at least 60%, at least 70%, at least 80%, at least 90%, including any value there between, of the appearance of the microorganism in a comparable situation lacking the presence of formulation or an article containing same. Alternatively, preventing means a reduction to at least 15%, 10%, or 5% of the appearance of the microorganism cells in a comparable situation lacking the presence of the formulation or an article containing same.

Methods for determining a level of appearance of a microorganism cells are known in the art.

General:

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed formulation, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.
General Procedure In additional exemplary procedures, the products were inoculated with 1—Bacteria: *Escherichia coli, Staphylococcus aureus* and *Pseudomonas aeruginosa,* 2—Yeast: *Candida albicans* and 3-Fungi: *Aspergillus brasiliensis* (*niger*). Each item of the 5 tested microorganism was inoculated by one of the 5 different microorganisms cited, as indicated in: USP 35, 2013, chapter: 51, Antimicrobial effectiveness testing.

Five samples of the product were inoculated with 1 microorganism each. The volume of the culture was calculated to yield a count of $10^5$-$10^6$ CFU/gr (CFU; colony-forming units).

The efficacy of was determined according to Antimicrobial Preservation Appendix XVI C. British, European Pharmacopea 2010.

In additional exemplary procedures, 20 gr sample from each item were tested 2, 7, 14, 21, and 28 days after inoculation.

In additional exemplary procedures, the test was also performed according to S.O.P 122: "Preservative Efficacy Challenge Test".

In additional exemplary procedure, minimum inhibitory concentration (MIC) evaluation test with *Candida albicans* was performed in test tubes. Growth in this case is visually evaluated. A pure culture of a single microorganism was grown in Tryptic soy broth, or sabouraud broth for yeast and mold.

In another exemplary procedure, MIC evaluation test with *A. niger* was performed in test tubes. Growth in this case is visually evaluated. A pure culture of a single microorganism was grown in Tryptic soy broth, or sabouraud broth for yeast and mold.

The culture is standardized using standard microbiological techniques to have a concentration of very near 1 million cells per milliliter.

The antimicrobial agent is diluted a number of times, with Tryptic soy broth or sabouraud broth for fungi. After the antimicrobial agent had been diluted, a volume of the standardized inoculums was added to each dilution vessel, bringing the microbial concentration to approximately 1,000,000 cells per milliliter. The inoculated, serially diluted antimicrobial agent was incubated at an appropriate temperature for the test organism, 24 hours for bacteria 48 for yeast and 72 for mold.

After incubation, the series of dilution vessels was observed for microbial growth, usually indicated by turbidity and/or a pellet of microorganisms in the bottom of the vessel. The last tube in the dilution series that does not demonstrate growth corresponds with the MIC of the antimicrobial agent. MIC results are expressed in ppm.

The microorganism strains used for the test were *E. coli* ATCC 8739, *P. aeruginosa* ATCC 9027, *S. aureus* ATCC 6538, *C. albicans* ATCC 10231, *A. niger* ATCC 16404.

Example 1

Anti Microbial Activity Evaluation

Exemplary formulations and antimicrobial results (MIC; relative efficacy) are presented in Table 1 below, showing the superior antimicrobial activity of the disclosed formulations.

TABLE 1

| Preservative | Microorganism | | | | |
| --- | --- | --- | --- | --- | --- |
| | S. aureus | E. coli | P. aeruginosa | A. niger | C. albicans |
| Maltol | 3800 | 4000 | <1350 | 3150 | 2250 |
| Ethyl Lauroyl Arginate | 500 | 2500 | 5000 | 20000 | 10000 |
| Maltol = 97% Ethyl Lauroyl Arginate = 3% | <300 | 400 | 600 | 600 | 400 |
| Maltol = 97% Stearamidopropyl dimethylamine = 3% | <360 | >1200 | 1200 | 720 | <360 |
| Maltol = 95% Stearamidopropyl dimethylamine = 5% | <360 | >1200 | 1200 | 720-960 | <360 |
| Maltol = 95% Hexadecylpyridinium chloride monohydrate = 5% | | <360 | 1200 | | |

TABLE 1-continued

| Preservative | S. aureus | E. coli | P. aeruginosa | A. niger | C. albicans |
|---|---|---|---|---|---|
| Maltol = 95%<br>Benzyldimethyldodecylammonium chloride = 5% | | <360 | 600 | | |
| Maltol = 97%<br>Benzyldimethyldodecylammonium chloride = 3% | <200 | 800 | 700 | 800 | 600 |
| Maltol = 95%<br>Hexadimethrine Bromide = 5% | | 600 | <360 | | |
| Maltol = 97%<br>Hexadimethrine Bromide = 3% | 600 | 1100 | 400 | 2000 | 1000 |
| Maltol = 95%<br>Cocoamidopropyl betaine = 5% | | >1200 | ~1200 | | |
| Maltol = 95%<br>Lauryl betaine = 5% | | >1200 | 1200 | | |
| Maltol = 95%<br>Hydroxycetyl hydroxyethyl dimonium chloride = 5% | | >1200 | >1200 | | |
| Maltol = 95%<br>Myristamidopropyl dimethylamine chloride = 5% | | 600 | 1200 | | |
| Maltol = 95%<br>N-[3-(Dimethylamino) propyl] lauramide = 5% | | 1200 | 1200 | | |
| Maltol = 95%<br>Hexadecyltrimethylammonium chloride = 5% | | <360 | 1200 | | |
| Maltol = 95%<br>Didecyldimethylammonium chloride = 5% | 22 | 45 | 180 | 22 | 22 |
| Maltol = 95%<br>Dimethyldioctylammonium chloride = 5% | 360 | 360 | 960 | 360-480 | <60 |
| Maltol = 95%<br>Dimethyldioctadecylammonium chloride = 5% | 720 | 960 | 600 | >1200 | >1200 |
| Maltol = 95%<br>Dodecyltrimethylammonium chloride = 5% | | 960 | 960 | | |
| Benzyldimethyldodecylammonium chloride | <60 | <60 | 120 | <60 | <60 |
| Didecyldimethylammonium chloride | <3 | <3 | 15 | <30 | <30 |
| Maltol = 95%<br>Didecyldimethylammonium chloride = 5% | 22 | 45 | 180 | 22 | 22 |
| Polyquaternium-2 | <60 | <60 | ~60 | 2000 | <60 |
| Polyquaternium-80 | 120 | 360 | >600 | 120 | 240 |
| Dodecyltrimethylammonium chloride | <60 | <60 | 360 | 360 | <60 |
| Maltol = 95%<br>Polyquaternium-2 = 2.5%<br>Didecyldimethylammonium chloride = 2.5% | <120 | <120 | 240 | 200 | <100 |
| Maltol = 95%<br>Polyquaternium-2 = 2.5%<br>Benzyldimethyldodecylammonium chloride = 2.5% | 360 | 480 | 720 | 400 | 100 |
| Maltol = 95%<br>Polyquaternium-2 = 2.5%<br>Dodecyltrimethylammonium chloride = 2.5% | | | | 1000 | |
| Maltol = 95%<br>DDAC = 5% (pH = 4) | <60 | <60 | <60 | 360-480 | <60 |
| Maltol = 95%<br>DDAC = 5% (pH = 5.5) | <60 | <60 | 360 | 120-360 | <60 |
| Maltol = 95%<br>DDAC = 5% (pH = 7) | <60 | 120 | 360 | 360 | 360 |
| Maltol = 95%<br>DDAC = 5% (pH = 9) | <60 | <60 | 120 | <60 | <60 |
| Maltol = 95%<br>Polyquaternium-80 = 5% | 480 | 480 | 1200 | 960 | 600 |
| Maltol = 95%<br>Polyquaternium-11 = 5% | >1200 | >1200 | >1200 | 1200 | <360 |
| Maltol = 95%<br>Polyquaternium-2 = 5% | 960-1200 | 960-1200 | 480 | ~1200-1300 | 480 |

Example 2

Preservative Effectiveness (Challenge Tests)

In another exemplary procedure, the antimicrobial preservative effectiveness was tested to measure the efficiency of the preservatives.

Method: The method applied was based on the USP 35 guidelines for antimicrobial effectiveness testing. Five samples of the product were inoculated with 1 microorganism each. The volume of the culture was calculated to yield a count of $10^5$-$10^6$ CFU/gr. A 4 weeks follow-up is performed. Each product was sampled once a week and a viable count was performed. Polysorbate 20 and Soy Lecithin were added to the culture media in order to neutralize the preservatives and to enable the recovery of all living microorganisms.

The antimicrobial tests are shown in Tables 2A-G.

In exemplary procedures, neutral base cream was preserved with 0.3% of a preservative comprising: maltol (95%), and didecyldimethylammonium chloride (5%).

The neutral base cream formulation comprises: water demineralized (82.8%), glycerin (4%), caprylic/capric triglycerides (3%), cetearyl glucoside and cetearyl alcohol (5%), cetearyl alcohol and Ceteareth-20 (4.8%), tocopheryl acetate (0.1%).

The results are summarized in Table 2A.

TABLE 2A

| Time of reading | E. Coli | S. Aureus | P. aeruginosa | C. albicans | A. niger |
|---|---|---|---|---|---|
| Inoculum | $1*10^6$ | $1*10^6$ | $1*10^6$ | $1*10^5$ | $1*10^5$ |
| 2 days | $6.7*10^4$ | $4.5*10^4$ | $6.5*10^3$ | $3*10^2$ | $6.4*10^3$ |
| 7 days | <10 | <10 | <10 | $4.1*10^3$ | $5.6*10^4$ |
| 14 days | <10 | <10 | <10 | $5.5*10^2$ | $8.8*10^3$ |
| 21 days | <10 | <10 | <10 | <10 | $8*10^3$ |
| 28 days | <10 | <10 | <10 | <10 | $8*10^3$ |

In additional exemplary procedures, neutral base cream was preserved with 0.3% of a preservative comprising: Maltol (95%), and benzyldimethyldodecylammonium chloride (5%).

The neutral base cream formulation comprises: water demineralized (82.8%), glycerin (4%), caprylic/capric triglycerides (3%), cetearyl glucoside and cetearyl alcohol (5%), cetearyl alcohol and Ceteareth-20 (4.8%), tocopheryl acetate (0.1%).

The results are summarized in Table 2B.

TABLE 2B

| Time of reading | E. Coli | S. Aureus | P. aeruginosa | C. albicans | A. niger |
|---|---|---|---|---|---|
| Inoculum | $1*10^6$ | $1*10^6$ | $1*10^6$ | $1*10^5$ | $1*10^5$ |
| 2 days | <10 | $3.1*10^3$ | $1.2*10^5$ | $8*10^2$ | $1*10^4$ |
| 7 days | $4.4*10^4$ | <10 | $1.3*10^5$ | $5.2*10^2$ | $6.7*10^4$ |
| 14 days | <10 | <10 | $5*10^3$ | <10 | $7*10^4$ |
| 21 days | <10 | <10 | <10 | <10 | $5.5*10^4$ |
| 28 days | <10 | <10 | <10 | <10 | $5*10^4$ |

In additional exemplary procedures, cationic conditioner preserved with 0.3% of a preservative comprising: maltol (95%), and didecyldimethylammonium chloride (5%). The cationic conditioner formulation comprises: water demineralized (85.7%), glycerin (3%), caprylic/capric triglycerides (3%), tetearyl glucoside and cetearyl alcohol (2%), cetearyl alcohol and Ceteareth-20 (5%), behetrimonium chloride (1%).

The results are summarized in Table 2C.

TABLE 2C

| Time of reading | E. Coli | S. Aureus | P. aeruginosa | C. albicans | A. niger |
|---|---|---|---|---|---|
| Inoculum | $1*10^6$ | $1*10^6$ | $1*10^6$ | $1*10^5$ | $1*10^5$ |
| 2 days | $1.1*10^5$ | $5.1*10^4$ | $7.3*10^3$ | $2.5*10^2$ | $3*10^4$ |
| 7 days | <10 | <10 | $5.2*10^3$ | $2.8*10^2$ | $5.5*10^4$ |
| 14 days | <10 | <10 | $3*10^2$ | <10 | $5.5*10^4$ |
| 21 days | <10 | <10 | <10 | <10 | $5*10^4$ |
| 28 days | <10 | <10 | <10 | <10 | $4.6*10^4$ |

In additional exemplary procedures, anionic shampoo was preserved with 0.3% of a preservative comprising: maltol (95%), and didecyldimethylammonium chloride (5%).

The anionic shampoo formulation comprises: water demineralized (78.8%), glycerin (0.3%), citric acid (0.1%), cocamidopropyl betaine (1%), cocamide diethanolamine (DEA) (1%), Sodium Laureth Sulphate (SLES) (15%), Sodium chloride (3.5%). The results are summarized in Table 2D.

TABLE 2D

| Time of reading | E. Coli | S. Aureus | P. aeruginosa | C. albicans | A. niger |
|---|---|---|---|---|---|
| Inoculum | $1*10^6$ | $1*10^6$ | $1*10^6$ | $1*10^5$ | $1*10^5$ |
| 2 days | $4.4*10^4$ | $3.5*10^3$ | $1*10^5$ | $3.5*10^4$ | $5.8*10^3$ |
| 7 days | <10 | <10 | <10 | $4.6*10^4$ | $2.8*10^4$ |
| 14 days | <10 | <10 | <10 | $3.3*10^3$ | $3.5*10^3$ |
| 21 days | <10 | <10 | <10 | <10 | $7*10^2$ |
| 28 days | <10 | <10 | <10 | <10 | $5*10^2$ |

In additional exemplary procedures, anionic shampoo was preserved with 0.4% of a preservative comprising: maltol (95%), didecyldimethylammonium chloride (2.5%) and Polyquaternium-2 (2.5%).

The anionic shampoo formulation comprises: water demineralized (78.7%), glycerin (0.3%), citric acid (0.1%), cocamidopropyl betaine (1%), cocamide diethanolamine (DEA) (1%), Sodium Laureth Sulphate (SLES) (15%), Sodium chloride (3.5%). The results are summarized in Table 2E.

TABLE 2E

| Time of reading | E. Coli | S. Aureus | P. aeruginosa | C. albicans | A. niger |
|---|---|---|---|---|---|
| Inoculum | 1*10^6 | 1*10^6 | 1*10^6 | 1*10^5 | 1*10^5 |
| 2 days | <10 | <10 | <10 | <10 | 3.3*10^4 |
| 7 days | <10 | <10 | <10 | <10 | 5.5*10^3 |
| 14 days | <10 | <10 | <10 | <10 | <10 |
| 21 days | <10 | <10 | <10 | <10 | <10 |
| 28 days | <10 | <10 | <10 | <10 | <10 |

It can be concluded that the tested product meets the EP and USP criteria for cosmetics.

In additional exemplary procedures, anionic shampoo was preserved with 0.5% of a preservative comprising: maltol (90%), and Polyquaternium-2 (10%).

The anionic shampoo formulation comprises: water demineralized (78.6%), glycerin (0.3%), citric acid (0.1%), cocamidopropyl betaine (1%), cocamide diethanolamine (DEA) (1%), Sodium Laureth Sulphate (SLES) (15%), Sodium chloride (3.5%). The results are summarized in Table 2F.

TABLE 2F

| Time of reading | E. Coli | S. Aureus | P. aeruginosa | C. albicans | A. niger |
|---|---|---|---|---|---|
| Inoculum | 1*10^6 | 1*10^6 | 1*10^6 | 1*10^5 | 1*10^5 |
| 2 days | <10 | <10 | <10 | <10 | 3.8*10^4 |
| 7 days | <10 | <10 | <10 | <10 | 3*10^2 |
| 14 days | <10 | <10 | <10 | <10 | 3*10 |
| 21 days | <10 | <10 | <10 | <10 | <10 |
| 28 days | <10 | <10 | <10 | <10 | <10 |

It can be concluded that the tested product meets the EP and USP criteria for cosmetics.

In additional exemplary procedures, anionic shampoo was preserved with 0.5% of a preservative comprising: maltol (90%), Polyquaternium-2 (5%) and Polyquaternium-80 (5%).

The anionic shampoo formulation comprises: water demineralized (78.6%), glycerin (0.3%), citric acid (0.1%), cocamidopropyl betaine (1%), cocamide diethanolamine (DEA) (1%), Sodium Laureth Sulphate (SLES) (15%), Sodium chloride (3.5%). The results are summarized in Table 2G.

TABLE 2G

| Time of reading | E. Coli | S. Aureus | P. aeruginosa | C. albicans | A. niger |
|---|---|---|---|---|---|
| Inoculum | 1*10^6 | 1*10^6 | 1*10^6 | 1*10^5 | 1*10^5 |
| 2 days | <10 | <10 | <10 | <10 | 4*10^4 |
| 7 days | <10 | <10 | <10 | <10 | 5*10^2 |
| 14 days | <10 | <10 | <10 | <10 | <10 |
| 21 days | <10 | <10 | <10 | <10 | <10 |
| 28 days | <10 | <10 | <10 | <10 | <10 |

It can be concluded that the tested product meets the EP and USP criteria for cosmetics. * The numbers in Tables 2A-C represent CFU/per 1 ml or per 1 mg; the tests of *E. coli, S. aureus*, and *P. aeruginosa* were performed at 30° C. The tests of *C. albicans, A. niger* were performed at 26° C.

Example 3

Anti Microbial Activity Evaluation and Preservative Effectiveness (Challenge Tests)

Exemplary formulations and antimicrobial results (MIC; relative efficacy) are presented. The antimicrobial preservative effectiveness of the disclosed formulations was tested to measure the efficiency of the preservatives.

Formulation 3A

Table 3 shows the antimicrobial activity results of formulation 3A.

TABLE 3

| Preservative | E. coli | S. aureus | P. aeruginosa | C. albicans | A. niger |
|---|---|---|---|---|---|
| Maltol = 95%, Polyquaternium-2 = 2.5%, Didecyldimethylammonium chloride (DDAC) = 2.5% | <120 | <120 | 240 | <100 | 200 |

In additional exemplary procedures, neutral base cream was preserved with 0.5% of a preservative comprising Formulation 3A, comprising: maltol (95%), Polyquaternium-2 (2.5%), and didecyldimethylammonium chloride (DDAC) (2.5%).

The neutral base cream formulation comprises: water demineralized (82.8%), glycerin (4%), caprylic/capric triglycerides (3%), cetearyl glucoside and cetearyl alcohol (5%), cetearyl alcohol and Ceteareth-20 (4.8%), tocopheryl acetate (0.1%).

The results are summarized in Table 4.

TABLE 4

| Time of reading | E. coli | S. aureus | P. aeruginosa | C. albicans | A. niger |
|---|---|---|---|---|---|
| Inoculum | $1 \times 10^6$ | $1 \times 10^6$ | $1.1 \times 10^6$ | $1 \times 10^5$ | $1 \times 10^5$ |
| 2 days | <10 | <10 | <10 | <10 | <10 |
| 7 days | <10 | <10 | <10 | <10 | <10 |
| 14 days | <10 | <10 | <10 | <10 | <10 |
| 21 days | <10 | <10 | <10 | <10 | <10 |
| 28 days | <10 | <10 | <10 | <10 | <10 |

In additional exemplary procedures, anionic shampoo was preserved with 0.4% of a preservative comprising Formulation 3A.

The anionic shampoo formulation comprises: water demineralized (78.7%), glycerin (0.30%), citric acid (0.1), cocamidopropyl betaine (10), cocamide diethanolamine (DEA) (10), Sodium Laureth Sulphate (SLES) (150%), Sodium chloride (3.50%).

The results are summarized in Table 5.

TABLE 5

| Time of reading | E. coli | S. aureus | P. aeruginosa | C. albicans | A. niger |
|---|---|---|---|---|---|
| Inoculum | $1 \times 10^6$ | $1 \times 10^6$ | $1.1 \times 10^6$ | $1 \times 10^5$ | $1 \times 10^5$ |
| 2 days | <10 | <10 | <10 | <10 | $3.3 \times 10^4$ |
| 7 days | <10 | <10 | <10 | <10 | $5.5 \times 10^3$ |
| 14 days | <10 | <10 | <10 | <10 | <10 |
| 21 days | <10 | <10 | <10 | <10 | <10 |
| 28 days | <10 | <10 | <10 | <10 | <10 |

Formulation 3B

Table 6 shows the antimicrobial activity results of formulation 3B.

TABLE 6

| Preservative | E. coli | S. aureus | P. aeruginosa | C. albicans | A. niger |
|---|---|---|---|---|---|
| Maltol = 90% Polyquaternium-80 = 10% | 480 | <240 | 1200 | 600 | 800 |

In additional exemplary procedures, anionic shampoo previously described was preserved with 0.5% of a preservative comprising Formulation 3B3, comprising: maltol (900%) and Polyquaternium-80 (100%).

The results are summarized in Table 7.

TABLE 7

| Time of reading | E. coli | S. aureus | P. aeruginosa | C. albicans | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | <10 | <10 | <10 | 10 | $4.5 \times 10^4$ |
| 7 days | <10 | <10 | <10 | <10 | $2.2 \times 10^2$ |
| 14 days | <10 | <10 | <10 | <10 | <10 |
| 21 days | <10 | <10 | <10 | <10 | <10 |
| 28 days | <10 | <10 | <10 | <10 | <10 |

In additional exemplary procedures, neutral base cream previously described was preserved with 0.5% of a preservative comprising Formulation 3B The results are summarized in Table 8.

TABLE 8

| Time of reading | E. coli | S. aureus | P. aeruginosa | C. albicans | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | 10 | <10 | 10 | <10 | $4.3 \times 10^4$ |
| 7 days | <10 | <10 | <10 | <10 | $6.7 \times 10^3$ |
| 14 days | <10 | <10 | <10 | <10 | $3 \times 10^1$ |
| 21 days | <10 | <10 | <10 | <10 | $2 \times 10^1$ |
| 28 days | <10 | <10 | <10 | <10 | <10 |

Formulation 3C

Table 9 shows the antimicrobial activity results of formulation 3C.

TABLE 9

| Preservative | E. coli | S. aureus | P. aeruginosa | C. albicans | A. niger |
|---|---|---|---|---|---|
| Maltol = 90% Polyquaternium-2 = 10% | 400 | <200 | 400 | 800 | 800 |

In additional exemplary procedures, neutral base cream previously described was preserved with 0.5% of a preservative comprising Formulation 3C, comprising: maltol (90%), and Polyquaternium-2 (10%).

The results are summarized in Table 10.

TABLE 10

| Time of reading | E. coli | S. aureus | P. aeruginosa | C. albicans | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | 10 | <10 | <10 | 10 | $6.3 \times 10^4$ |
| 7 days | <10 | <10 | <10 | <10 | $8.5 \times 10^3$ |
| 14 days | <10 | <10 | <10 | <10 | $5.3 \times 10^2$ |
| 21 days | <10 | <10 | <10 | <10 | $2.1 \times 10^2$ |
| 28 days | <10 | <10 | <10 | <10 | $5 \times 10^1$ |

In additional exemplary procedures, anionic shampoo previously described was preserved with 0.5% of a preservative comprising Formulation C.

The results are summarized in Table 11.

TABLE 11

| Time of reading | E. coli | S. aureus | P. aeruginosa | C. albicans | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | <10 | <10 | <10 | <10 | $3.8 \times 10^4$ |
| 7 days | <10 | <10 | <10 | <10 | $3 \times 10^2$ |
| 14 days | <10 | <10 | <10 | <10 | $3 \times 10^1$ |
| 21 days | <10 | <10 | <10 | <10 | <10 |
| 28 days | <10 | <10 | <10 | <10 | <10 |

Formulation 3D

Table 12 shows the antimicrobial activity results of formulation 3D.

TABLE 12

| Preservative | E. coli | S. aureus | P. aeruginosa | C. albicans | A. niger |
|---|---|---|---|---|---|
| Maltol = 95%<br>Polyquaternium-80 = 2.5%<br>Didecyldimethylammonium chloride (DDAC) = 2.5% | <100 | 200 | 400 | <100 | 400 |

In additional exemplary procedures, neutral base cream previously described was preserved with 0.5% of a preservative comprising Formulation 3D, comprising: maltol (95%), didecyldimethylammonium chloride (DDAC) (2.5%), and Polyquaternium-80 (2.5%).

The results are summarized in Table 13.

TABLE 13

| Time of reading | E. coli | S. aureus | P. aeruginosa | C. albican | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | <10 | <10 | <10 | <10 | <10 |
| 7 days | <10 | <10 | <10 | <10 | <10 |

TABLE 13-continued

| Time of reading | E. coli | S. aureus | P. aeruginosa | C. albican | A. niger |
|---|---|---|---|---|---|
| 14 days | <10 | <10 | <10 | <10 | <10 |
| 21 days | <10 | <10 | <10 | <10 | <10 |
| 28 days | <10 | <10 | <10 | <10 | <10 |

In additional exemplary procedures, anionic shampoo previously described was preserved with 0.5% of a preservative comprising Formulation 3D.

The results are summarized in Table 14.

TABLE 14

| Time of reading | E. coli | S. aureus | P. aeruginosa | C. albicans | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | <10 | <10 | <10 | <10 | $1 \times 10^4$ |
| 7 days | <10 | <10 | <10 | <10 | 10 |
| 14 days | <10 | <10 | <10 | <10 | <10 |
| 21 days | <10 | <10 | <10 | <10 | <10 |
| 28 days | <10 | <10 | <10 | <10 | <10 |

Formulation 3E

Table 15 shows the antimicrobial activity results of formulation 3E.

TABLE 15

| Preservative | E. coli | S. aureus | P. aeruginosa | C. albicans | A. niger |
|---|---|---|---|---|---|
| Maltol = 95%,<br>Didecyldimethylammonium chloride (DDAC) = 5% | <50 | <50 | 100 | <50 | 100 |

In additional exemplary procedures, anionic shampoo previously described was preserved with 0.5% of a preservative comprising Formulation 3E comprising: maltol (95%), and didecyldimethylammonium chloride (DDAC) (5%).

The results are summarized in Table 16.

TABLE 16

| Time of reading | E. coli | S. aureus | P. aeruginosa | C. albicans | A. niger |
|---|---|---|---|---|---|
| Inoculum | $1.1 \times 10^6$ | $1 \times 10^6$ | $1 \times 10^6$ | $1.1 \times 10^5$ | $1 \times 10^5$ |
| 2 days | $1 \times 10^5$ | $4.8 \times 10^3$ | $3 \times 10^4$ | $1.5 \times 10^2$ | $5.5 \times 10^3$ |
| 7 days | <10 | $2 \times 10^1$ | $1 \times 10^2$ | $2 \times 10^1$ | $6 \times 10^3$ |
| 14 days | <10 | <10 | <10 | <10 | $6.5 \times 10^3$ |
| 21 days | <10 | <10 | <10 | <10 | $3.6 \times 10^3$ |
| 28 days | <10 | <10 | <10 | <10 | $3 \times 10^3$ |

Formulation 3F

Table 17 shows the antimicrobial activity results of formulation 3F.

TABLE 17

| Preservative | E. coli | S. aureus | P. aeruginosa | C. albicans | A. niger |
|---|---|---|---|---|---|
| Maltol = 90%,<br>Suga Quat L-1010 (LAURDIMONIUMHYDROXYPROPYL DECYLGLUCOSIDES CHLORIDE) = 10% | 200 | <100 | 1000 | 300 | 400 |

In additional exemplary procedures, anionic shampoo previously described was preserved with 0.5% of a preservative comprising Formulation 3F comprising: maltol (90%), and Suga Quat L-1010 (LAURDIMONIUMHYDROXYPROPYL DECYLGLUCOSIDES CHLORIDE) (10%)

The results are summarized in Table 18.

TABLE 18

| Time of reading | E. coli | S. aureus | P. aeruginosa | C. albicans | A. niger |
|---|---|---|---|---|---|
| Inoculum | $2.3 \times 10^5$ | $1.3 \times 10^5$ | $1 \times 10^5$ | $3 \times 10^4$ | $1 \times 10^4$ |
| 2 days | $2 \times 10^3$ | <10 | <10 | <10 | $1.7 \times 10^3$ |
| 7 days | $1 \times 10^3$ | <10 | <10 | <10 | $1.5 \times 10^1$ |

TABLE 18-continued

| Time of reading | E. coli | S. aureus | P. aeruginosa | C. albicans | A. niger |
|---|---|---|---|---|---|
| 14 days | 10 | <10 | <10 | <10 | 10 |
| 21 days | <10 | <10 | <10 | <10 | <10 |
| 28 days | <10 | <10 | <10 | <10 | <10 |

Formulation 3G

Table 19 shows the antimicrobial activity results of formulation 3G comprising: maltol (90%), and Cola Lipid C (Cocamidopropyl PG-Dimonium Chloride Phosphate) (10%).

TABLE 19

| Preservative | E. coli | S. aureus | P. aeruginosa | C. albicans | A. niger |
|---|---|---|---|---|---|
| Maltol = 90% Cola lipid C = 10% | 480 | 960 | 1200 | 480 | 960 |

In another exemplary procedure, the antimicrobial preservative effectiveness is tested to measure the efficiency of the preservative.

Example 4

Anti Microbial Activity Evaluation and Preservative Effectiveness (Challenge Tests)

Further formulations comprising Maltol 90% to 98% and one or more of the following cationic surfactants 1) to 12) is prepared: 1) Berberine CAS: 2086-83-1; 2) Berberrubine; 3) *Berberis vulgaris* root extract CAS: 84649-92-3/8054-40-8; 4) Isopropylbenzyl butylnorberberine iodide; 5) Palmatine cas: 3486-67-7; 6) Jatrorrhizine; 7) Coptisine; 8) Ungeremine; 9) Epiberberine; 10) Pseudoberberine; 11) Stepharanine; 12) Sinapine After determining the antimicrobial results (MIC; relative efficacy) of each formulation, the antimicrobial preservative effectiveness of the disclosed formulations is tested as previously described to measure the efficiency of the preservatives.

In another exemplary procedure, the antimicrobial preservative effectiveness was tested to measure the efficiency of the preservatives.

Example 5

Maltol Shielding

Maltol has a metal chelating property. It can bond with metal ions and form a chelate product that can be strongly colored. This reaction is highly likely to happen when maltol is used in a manufacturing process involving steel based equipment. It means that even small quantities of these chelates could induce an undesirable color in a finished cosmetic product.

A way to inhibit this phenomenon would be to add to maltol a small quantity of a stronger chelating agent, in order to intercept possible metal ions before Maltol could do so. Thus, an examination of various chelating agents in order to "protect" the Maltol from chelating metal ions was done.

Procedure: To a 0.5% solution of 90% Maltol and 10% Polyquaternium-80 in demineralized water a chelating agent was added in concentrations of 25 ppm, 50 ppm, 100 ppm, 150 ppm, 200 ppm and 250 ppm, then a chip of stainless steel 316 (~1×1 cm) was added to the solution for 12 hr.

The following chelating agents were tested: 1) Disodium EDTA—Ethylenediaminetetraacetic acid disodium salt; 2) EDTMP—Ethylenediamine tetra (methylene phosphonic acid); 3) Alanine di-acetic acid; 4) Ascorbic acid; 5) Sodium Gluconate; 6) Zinc gluconate; 7) Vanillin; 8) Sodium vanillate; 9) Ethylenediamine-N,N-discuccinic acid trisodium salt (Natrlquest E30).

The absorbance at 410 nm was measured with spectrophotometer Genesys 10uv (Thermo Scientific), the blank was a solution of 0.5% 90% Maltol and 10% Polyquaternium-80 in demineralized water.

Figure 1:
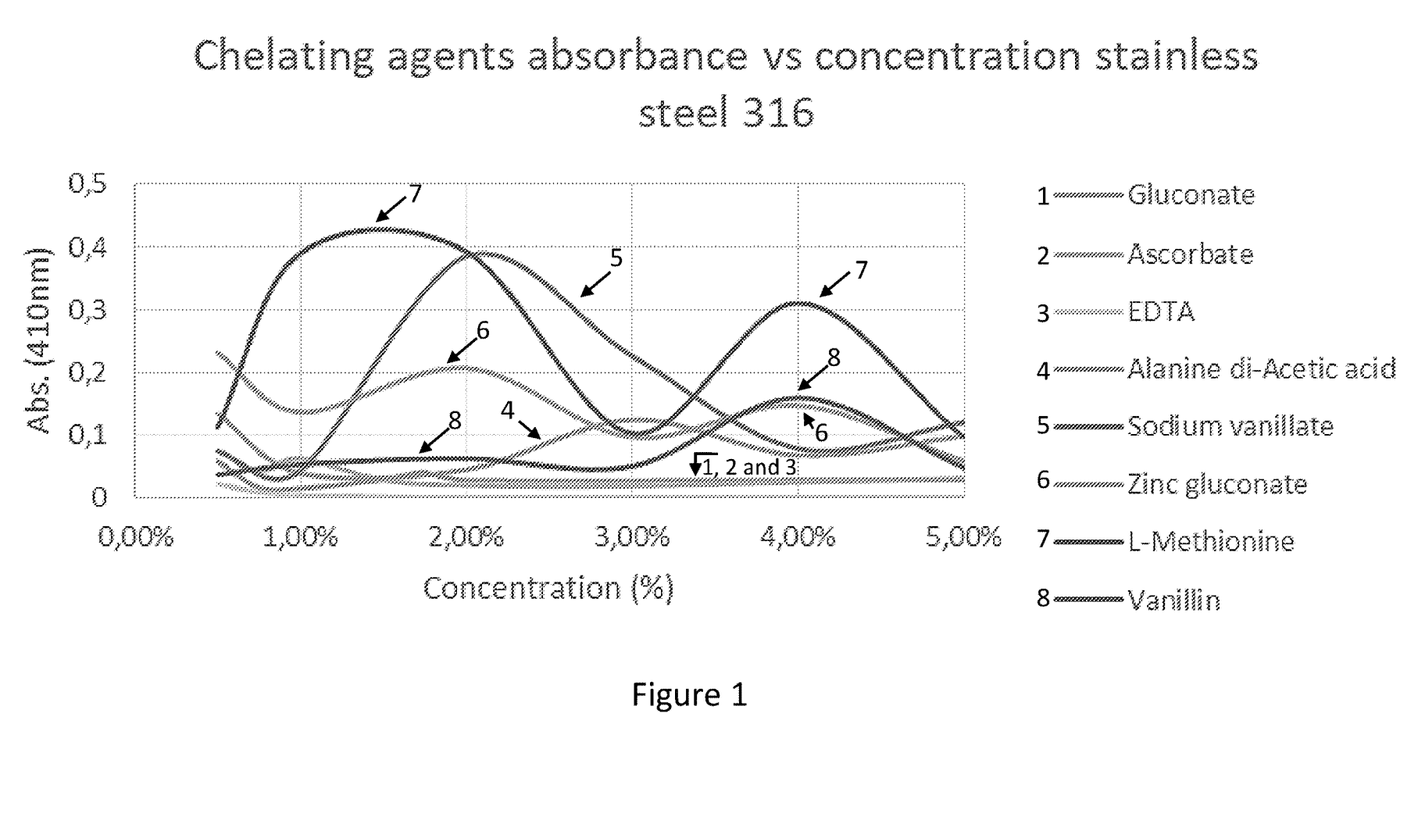
FIG. 1 Presents a graph showing the effect of different chelators in a formulation on stainless steel 316.

The results with different chelators on stainless steel 316 are summarized in Table 20 and FIG. 1.

TABLE 20

| | Concentration (%) | | | | | |
|---|---|---|---|---|---|---|
| Chelator | 0.5 | 1 | 2 | 3 | 4 | 5 |
| Disodium EDTA | 0.022 | 0.009 | 0.004 | 0.002 | 0 | 0 |
| Beta Alanine diAcetic acid | 0.133 | 0.039 | 0.045 | 0.124 | 0.067 | 0.098 |
| Sodium gluconate | 0.022 | 0.04 | 0.042 | 0.045 | 0.005 | 0.006 |
| Ascorbic acid | 0.182 | 0.162 | 0.145 | 0.155 | 0.101 | 0.06 |
| Sodium vanillate | 0.073 | 0.044 | 0.386 | 0.226 | 0.078 | 0.12 |
| Zinc gluconate | 0.231 | 0.136 | 0.207 | 0.096 | 0.147 | 0.058 |
| L-Methionine | 0.113 | 0.391 | 0.393 | 0.102 | 0.311 | 0.096 |
| Vanillin | 0.037 | 0.053 | 0.062 | 0.05 | 0.159 | 0.048 |

Figure 2:
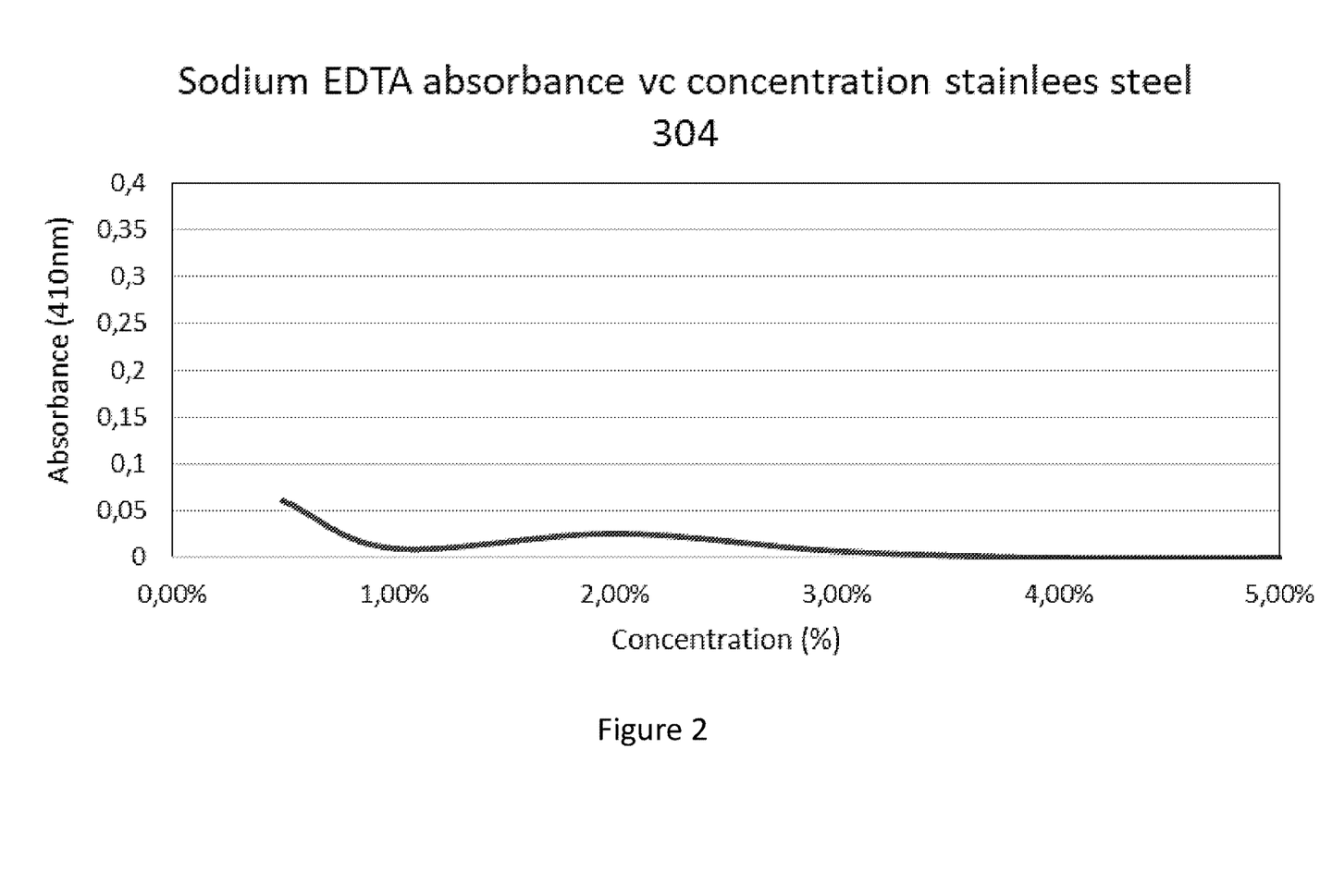
FIG. 2 presents a graph showing the effect of a formulation with disodium EDTA on stainless steel 304.

The results with disodium EDTA on stainless steel 304 are summarized in Table 21 and FIG. 2.

TABLE 21

| | Concentration (%) | | | | | |
|---|---|---|---|---|---|---|
| Chelator | 0.5 | 1 | 2 | 3 | 4 | 5 |
| Disodium EDTA | 0.061 | 0.010 | 0.026 | 0.007 | 0 | 0 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A composition comprising an antimicrobial agent consisting of a pyrone and at least one cationic surfactant in a ratio that ranges from 70:30 to 99:1 by weight, respectively; wherein said composition is characterized by a antimicrobial activity when applied to a product selected from a cosmetic product, and a pharmaceutical product, so as to obtain an amount of said antimicrobial agent within said product ranging between 0.2-1% w/w;

wherein said pyrone comprises maltol, ethyl maltol or any derivative thereof comprising a pyrone ring and having at least 80% antimicrobial activity of maltol when combined with the at least one cationic surfactant, and wherein the antimicrobial activity is determined according to Antimicrobial Preservation Appendix XVI C. British, European Pharmacopea 2010;

wherein said at least one at least one cationic surfactant is a quaternary ammonium compound, or is a mixture of the quaternary ammonium compound and a tertiary ammonium compound.

2. The composition of claim 1, wherein said pyrone is selected from maltol and ethyl maltol.

3. The composition of claim 1, wherein said quaternary ammonium compound is a monomeric compound.

4. The composition of claim 1, wherein said at least one at least one cationic surfactant is a quaternary ammonium compound; and wherein said quaternary ammonium compound quaternary ammonium cation is represented by Formula: $NR_4^+$, wherein each R is independently selected from an alkyl group, an aryl group or a combination thereof.

5. The composition of claim 1, wherein said antimicrobial activity comprises microbial load reduction of at least one microbe selected from *Escherichia coli, Staphylococcus aureus Pseudomonas aeruginosa, Candida albicans* and *Aspergillus brasiliensis*; and wherein the microbial load reduction is determined according to Antimicrobial Preservation Appendix XVI C. British, European Pharmacopea 2010.

6. The composition of claim 1, wherein said quaternary ammonium compound is selected from the group consisting of: benzyldimethyldodecylammonium chloride, didecyldimethylammonium chloride, dodecyltrimethylammonium chloride, hexadecyltrimethylammonium chloride, Polyquaternium-2, Polyquaternium-80, Polyquaternium-11, Polyquaternium-52, Polyquaternium-17, Sodium Cocamidopropyl PG-Dimonium Chloride Phosphate, Dihexadecyl dimethyl ammonium chloride Laurdimoniumhydroxypropyl decylglucoside chloride, Berberine, Berberrubine, *Berberis vulgaris* root extract, Isopropylbenzyl butylnorberberine iodide, Palmatine, Jatrorrhizine, Coptisine, Ungeremine, Epiberberine, Pseudoberberine, Stepharanine, Sinapine, including any salt and any combination thereof.

7. The composition of claim 1, in the form of a powder or a solution.

8. The composition of claim 1, being an antimicrobial formulation.

9. The composition of claim 1, further comprising a chelating agent, or a salt thereof.

10. The composition of claim 9, wherein said chelating agent is selected from the group consisting of: Disodium EDTA-Ethylenediaminetetraacetic acid disodium salt, EDTMP—Ethylenediamine tetra (methylene phosphonic acid), Alanine di-acetic acid, Ascorbic acid, Sodium Gluconate, Zinc gluconate, Vanillin, Ethylenediamine-N,N-discuccinic acid trisodium salt, pentetic acid (DTPA), and any combination thereof.

* * * * *